United States Patent [19]

Smith et al.

[11] Patent Number: 5,262,080

[45] Date of Patent: Nov. 16, 1993

US005262080A

[54] LITHIUM ALKOXIDE REAGENT COMPOSITIONS

[76] Inventors: W. Novis Smith, 412 S. Perth St., Philadelphia, Pa. 19147; Jessica Godshall, 3878 T. Lancaster Ave., Philadelphia, Pa. 19104

[21] Appl. No.: 737,651

[22] Filed: Jul. 30, 1991

[51] Int. Cl.$^5$ ............................................. C09K 3/00
[52] U.S. Cl. ............................................. 252/182.12
[58] Field of Search ................................. 252/182.12

[56] References Cited

U.S. PATENT DOCUMENTS

| | | | |
|---|---|---|---|
| 3,897,518 | 7/1975 | Koppel | 558/179 |
| 3,899,508 | 8/1975 | Wikel | 548/374.1 |
| 4,748,283 | 5/1988 | Komienski | 568/851 |
| 5,136,033 | 8/1992 | Masilamani et al. | 540/468 |

OTHER PUBLICATIONS

Bradley et al., *Metal Alkoxides*, pp. 10–11, Academic Press (1978) New York.

*Primary Examiner*—Edward A. Miller
*Attorney, Agent, or Firm*—John Lezdey

[57] ABSTRACT

A method for the preparation o a reagent composition containing lithium alkoxide of the formula: LiOR, wherein R is an alkyl group of 4 to 20 carbon atoms which comprises the steps of reacting lithium metal particles with an alcohol of the formula ROH, wherein R is as hereinbefore defined, in a solvent. The alcohol is present in an amount of not more than 20%, so that the solution composition can be used without isolation in a suitable reaction.

7 Claims, No Drawings

LITHIUM ALKOXIDE REAGENT COMPOSITIONS

FIELD OF THE INVENTION

The present invention relates to a method for preparing lithium alkoxide reagent compositions having a greater concentration of lithium alkoxide available for a chemical reaction. More particularly, there is provided a lithium alkoxide composition which is useful for selectivity in reactions and require lesser amounts of solvents. Also provided is the increase of the lithium alkoxide concentration in a reagent compositions by the use of a lithium alkoxide cosolvent.

BACKGROUND OF THE INVENTION

Lithium alkoxides bridge the gaps between organic and inorganic chemistry and are growing increasingly important. Lithium alkoxides are useful as catalysts for a wide variety of polymerization reactions and for esterifications, condensation and isomerization processes, for example, the preparation of lithium ethylene glycoxide by adding a stoichiometric amount of lithium t-butoxide to excess ethylene glycol.

The lithium alkoxides are generally prepared from lithium metal and an excess of the parent alcohol and sold in their pure or purified form to be dissolved in the solvent used for a selected reaction. However, isolation and purification for subsequent use increases the cost of the catalyst. Moreover, subsequent dissolution in solvents for the reaction has generally required the use of a large amount of solvent in order to obtain a sufficient amount of catalyst in solution to obtain a desired yield. It therefore would be advantageous to prepare a catalyst reagent composition which does not require isolation and/or purification of the catalyst and wherein the reagent composition can be used directly in a desired reaction. It is even more preferable if the reagent composition contains a high concentration of the catalyst and a minimal excess of alcohol.

Lithium t-butoxide is a popular compound for use in metalation and as a catalyst in organic synthesis. It is moderately soluble in hydrocarbon synthesis, e.g. about 1.35M in toluene. In fact, it is only soluble at about 2.3M in tetrahydrofuran which is its best solvent. However, in metalation reactions better yields can be obtained with high concentrations of lithium alkoxides.

When using a concentrated solution of lithium alkoxides, it is desirable to use concentrated solutions to minimize the amount of additional solvents being added to the reactor.

U.S. Pat No. 3,761,529 discloses a method of purifying lithium alkoxides which are prepared from lithium metal wire and an excess of alcohol in tetrahydrofuran. The objective of the patent is to prepare and then isolate the lithium alkoxides. One of the problems in the process disclosed is that the presence of a large excess of alcohol reduces the solubility of the alkoxide prepared and contributes to the presence of impurities.

It is an object of the invention to provide a means for making available high concentrations of lithium alkoxides for use in reactions.

It is a further object of the invention to provide lithium alkoxide in solution.

It is a yet further object to provide increased concentrations of lithium alkoxides in ether—free solvents.

SUMMARY OF THE INVENTION

The present invention provides for the preparation of a reagent composition containing a lithium alkoxide of the formula; LiOR, wherein R is an alkyl group of 4 to 20 carbon atoms. The process of the invention involves the reaction of lithium particles in a solvent with an alcohol of the formula: ROH, wherein R is as hereinbefore defined. It is critical in the process that the alcohol is not present in an amount of more than 20% by weight of the stoichiometric amount required.

The reagent composition prepared by the invention has a concentration of at least 1.3M, preferably about 2.1M.

The preferred solvent for the process and reagent is tetrahydrofuran. However, the solvent can comprise an aliphatic or monocyclic aliphatic hydrocarbon, or example, pentane, hexane, cyclohexane and cyclopentane.

The present invention also provides a process for increasing the solubility of relatively insoluble lithium branched alkoxides in solvents by incorporating in the solvent a second more soluble lithium branched alkoxide. The second lithium branched alkoxide can be added to the prepared lithium alkoxide reagent composition or prepared simultaneously therewith.

Lithium branched alkoxides having four or more carbon atoms and are branched in the alpha or beta positions are particularly important in a reagent composition. The tertiary alkoxide group is considered having the highest basicity and the most selective because of the steric interaction of the three alkyl groups on the carbon atom bound to the oxygen of the alkoxide group. It is preferable to use as the solubilizing alkoxide those alkoxides which have similar basicity as the primary lithium alkoxide. That is, for lithium t-alkoxides, the solubilizing agent would be another lithium t-alkoxide. For a lithium sec-alkoxide, another lithium sec-alkoxide would be utilized.

The addition of the second lithium alkoxide not only improves the solubility of the primary lithium alkoxide but prevents post precipitation thereof.

An amount of about to 50 mole % of the second lithium alkoxide can be used to increase the alkoxide concentration of the reagent composition.

DESCRIPTION OF THE PREFERRED EMBODIMENTS

In accordance with one embodiment of the invention a lithium alkoxide reagent composition ready for use in a further reaction, for example, an esterification reaction or metalation reaction, without the need to purify the composition prior to use. A reagent composition is prepared by reacting lithium particles, which are placed in a suitable solvent, with an alkanol having 4 to 20 carbon atoms.

The solvent is preferably tetrahydrofuran, however, aliphatic or monocyclic aliphatic hydrocarbons can be used alone or in combination with tetrahydrofuran. The choice of solvent will be based upon the subsequent reaction in which the reagent composition will be employed.

It is well known that alkoxides have limited degrees of solubility with different hydrocarbon solvents. Furthermore, it is preferable for large scale production to have high concentrations of reagents in a minimum amount of solvent. According to the invention the concentration of lithium branched alkoxides can be increased by providing a further lithium branched alkoxide in the solvent. The additional lithium branched alkoxide can be initially present, added any time, or prepared simultaneously with the primary lithium alkoxide.

A preferred feature of this embodiment is the preparation of lithium t-butoxide reagent composition or a reagent which behaves and reacts similarly. It has been found that lithium t-pentoxide will form very concentrated solutions with lithium t-butoxide in aliphatic and/or aromatic solvents. This permits the use of the reagent composition directly without isolation in reactions of compounds that are primarily soluble in aliphatic or aromatic solvents. Solutions having concentrations of the lithium alkoxides of from 2.5 to 3.5 molar can be prepared. The mixture of alkoxides is particularly useful in metalation reactions.

Also, in preparing the mixed alkoxides the alcohols should not be in excess of more than 20%, preferably 10% of the stoichiometric amount because the excess alcohols reduce solubility and create impurities.

The hydrocarbon solvents which may be used in the invention include the monocyclic aromatic solvents such as benzene, toluene, xylene, cumene, etc., the aliphatic solvents such as pentane, hexane, etc, and the monocyclic aliphatic solvents such as cyclohexane, cycloheptane, cyclopentane, etc. The following examples are illustrative of the practice of the method of the present invention. It will be understood; however, that is not to be construed as in any way limitative of the full scope of the invention since various changes can be made, without departing from the spirit of the teaching contained herein, in the light of the guiding principles which have been set forth about. All percentages herein stated are based on weight except wherein noted.

Example 1

Preparation of Lithium Tertiary Butoxide

To a three-necked flask under argon and equipped with a oil leg bubbler, were added 5.6 g (0.8 moles) lithium metal powder and 300 ml of tetrahydrofuran (THF). The slurry was stirred under argon and heated to 40° C. and 63 g (0.85 moles) of tertiary butanol in 20 ml THF (to depress the freezing point) were added over a one-hour period. (Care is taken not to add more than 10% of the alcohol until it is certain that the reaction has initiated.) The temperature is permitted to rise to 50° C. and the reaction is run at this temperature with some cooling. After the addition is complete, the reaction is maintained at this temperature for another 3–4 hours and then cooled to room temperature. The clear translucent solution may be used as is. The concentration is about 2. 1M and the yield is quantitative.

Example 2

Preparation of Lithium Tertiary Butoxide

To a three-necked flask under argon and equipped with an oil leg bubbler, were added 5.6 g (0.8 moles) lithium metal powder and 140 ml THF. This slurry was stirred and heated to 40° C. and 63 g (0.85 moles) of tertiary butanol containing 20 ml THF were added over a one-hour period. (Care is taken not to added more than 10% of the alcohol until it is certain that the reaction has initiated.) the temperature is permitted to rise to 50° C. and the reaction maintained at this temperature. When the addition has been completed, the reaction is maintained at 50° C. for 3–4 hours and then an additional 160 ml THF are added. The final solution is a clear to translucent pale yellow to amber solution of about 2.1M lithium tertiary butoxide in THF in quantative yield. The final concentration is then adjusted to 2.1–2.2M.

Example 3

Preparation of Lithium Tertiarypentoxide

Following the procedure of Example 2, 114.6 g (1.3 moles) tertiary pentanol was added to 9.0 g (1.3 moles) lithium metal powder in 250 ml of THF. The final solution was light yellow and had a concentration of 3.2M lithium tertiary pentoxide.

Example 4

Preparation of Lithium Tertiarypentoxide

Following the procedure of Example 2, except that 275 ml cyclohexane was used as solvent, a final clear yellow solution was obtained which had a concentration of 3.1M of lithium tertiary pentoxide.

Example 5

Preparation of Mixed Lithium TertiaryPentoxide/Tertiary Butoxide

Following the procedure of Example 1, except there was added a mix of 48 g (0.65 moles) of tertiary butanol and 62 g (0.7 moles) tertiary pentanol to 9.0 g (1.3 moles) of lithium metal powder in 300 ml THF. The final solution had a concentration of 2.85M of the mixed lithium alkoxides.

What is claimed is:

1. A method for the preparation of a reagent composition containing a lithium alkoxide selected from the group consisting of lithium tertiary butoxide, lithium tertiary pentoxide, and mixtures thereof, which comprises the steps of reacting lithium particles with a suitable alcohol selected from the group consisting of tertiary butanol, tertiary pentanol and mixtures thereof in a solvent selected from the group consisting of tetrahydrofuran, aliphatic hydrocarbon of 5 or 6 carbon atoms and monocyclic aliphatic hydrocarbon of 5 or 6 carbon atoms, said alcohol being present in an amount of not more than 20% of the stoichiometric amount, whereby said composition can be used without isolation in a subsequent reaction.

2. The method of claim 1 wherein said alcohol is tertiary butanol and lithium tertiary butoxide is prepared.

3. The method of claim 1 wherein said alcohol is tertiary pentanol and lithium tertiary pentoxide is prepared.

4. A reagent composition prepared by the process of claim 1.

5. A reagent composition prepared by the process of claim 2.

6. A reagent composition prepared by the process of claim 3.

7. A method for the preparation of a reagent composition containing a lithium alkoxide selected from the group consisting of lithium tertiary butoxide, lithium tertiary pentoxide, and mixtures thereof, which comprises the steps of reacting lithium metal particles with a suitable alcohol selected from the group consisting of tertiary butanol, tertiary pentanol and mixtures thereof in a solvent selected from the group consisting of tetrahydrofuran, aliphatic hydrocarbon of 5 or 6 carbon atoms and monocyclic aliphatic hydrocarbon of 5 or 6 carbon atoms, said alcohol being present in an amount of not more than 10% of the stoichiometric amount, whereby said composition can be used without isolation in a subsequent reaction.

* * * * *